US00PP18512P3

(12) United States Plant Patent
McDonald

(10) Patent No.: US PP18,512 P3
(45) Date of Patent: Feb. 26, 2008

(54) APPLE TREE NAMED 'EL NIÑO'

(50) Latin Name: *Malus domestica*
Varietal Denomination: El Niño

(76) Inventor: Steven A. McDonald, 13321 R. I SW, Royal City, WA (US) 98357

( * ) Notice: Subject to any disclaimer, the term of this patent is extended or adjusted under 35 U.S.C. 154(b) by 0 days.

(21) Appl. No.: 11/501,205

(22) Filed: Aug. 7, 2006

(65) Prior Publication Data

US 2007/0044182 P1 Feb. 22, 2007

Related U.S. Application Data

(60) Provisional application No. 60/709,892, filed on Aug. 19, 2005.

(51) Int. Cl.
*A01H 5/00* (2006.01)

(52) U.S. Cl. ..... Plt./162

(58) Field of Classification Search ..... Plt./162
See application file for complete search history.

*Primary Examiner*—Kent Bell
(74) *Attorney, Agent, or Firm*—Klarquist Sparkman LLP

(57) ABSTRACT

A new and distinctive variety of an apple tree, named 'El Niño' characterized by fruit color having intense dark red stripes over a bright red background.

4 Drawing Sheets

CROSS REFERENCE TO RELATED APPLICATION

The entire disclosure of the provisional application is considered to part of the disclosure of the following application and is hereby incorporated by reference herein.

Latin name of the genus and species of the plant claimed: *Malus domestica.*

Variety denomination: 'El Niño'.

BACKGROUND OF THE INVENTION

'El Niño Gala' was originally found by Steven A. McDonald as a bud sport of a tree growing in a cultivated area in his orchard, commonly known as Royal T Farms, 13321 Rd I SW, Royal City, Wash. The original plant originated as a bud sport that had been grown by grafting 'Royal Gala' (expired U.S. Plant Pat. No. 4,121) budwood to a Mark rootstock in 1991. More specifically, a number of 'Kidd's Gala' trees growing on Mark rootstock were damaged during a storm. These trees with Mark rootstock were each budded with 'Royal Gala' budwood. The resulting original plant of my new variety grew from one of these 'Royal Gala' budwood grafts. The new tree grew unnoticed until 1996 when the distinct red color of its fruit was apparent.

This new and distinct 'El Niño' tree variety has not been observed under all possible environmental conditions. The phenotype may vary significantly with variations in environment such as temperature, light intensity and day length, without any variation in genotype. However, the distinctive combination of traits set forth in the description below have been repeatedly observed in the original tree and in asexually propagated progeny and have been determined to be firmly fixed and to be the basic characteristics of this new tree, which in combination distinguishes 'El Niño' as a new and distinct variety.

The new variety has been asexually propagated by or at the direction of Steven A. McDonald by grafting onto Emla 26 rootstock. Asexual propagation has been performed at the Royal T Farms in Royal City, Wash.

BRIEF SUMMARY OF THE INVENTION

The 'El Niño' variety is distinguished from other apple varieties due to the following unique combination of characteristics:

1. Achieves excellent fruit color with intense dark red stripe over a bright red background.
2. Color is consistent on applies throughout the tree.

The following detailed description is from observations of the original 'El Niño' tree and from observations of approximately seven year old asexually propagated 'El Niño' progeny that were observed growing in a cultivated area in Royal City, Grant County, Wash. Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (RHS) Colour Chart.

BRIEF DESCRIPTION OF THE PHOTOGRAPHS

DETAILED BOTANICAL DESCRIPTION

Figure 1:
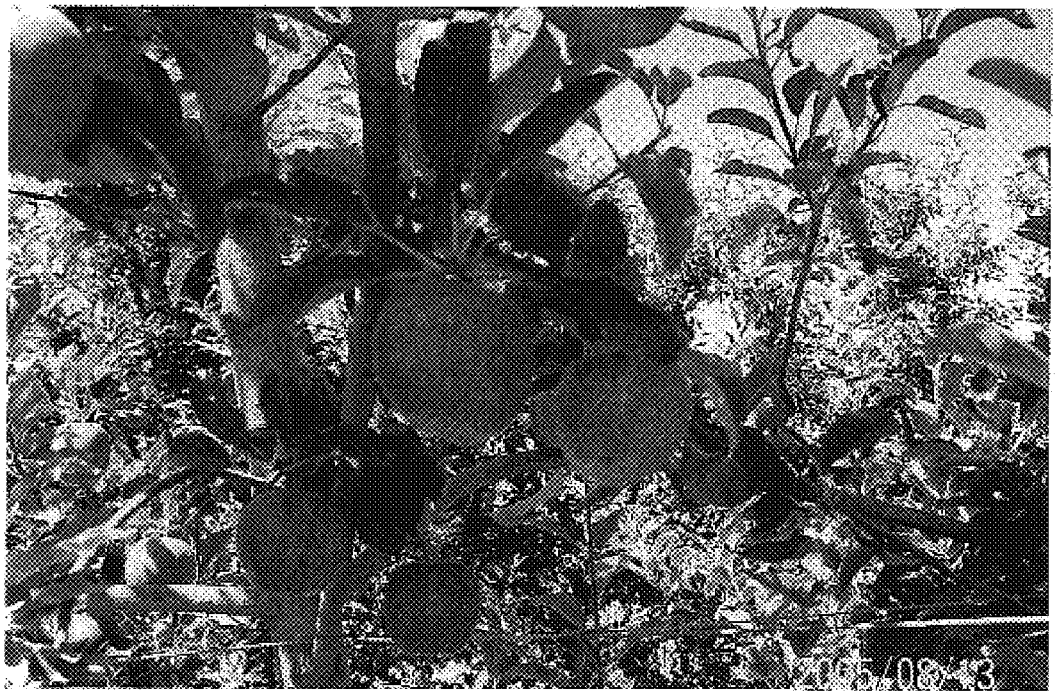
FIG. 1 shows the fruit on one of the new 'El Niño' Gala apple trees.
Figure 2:
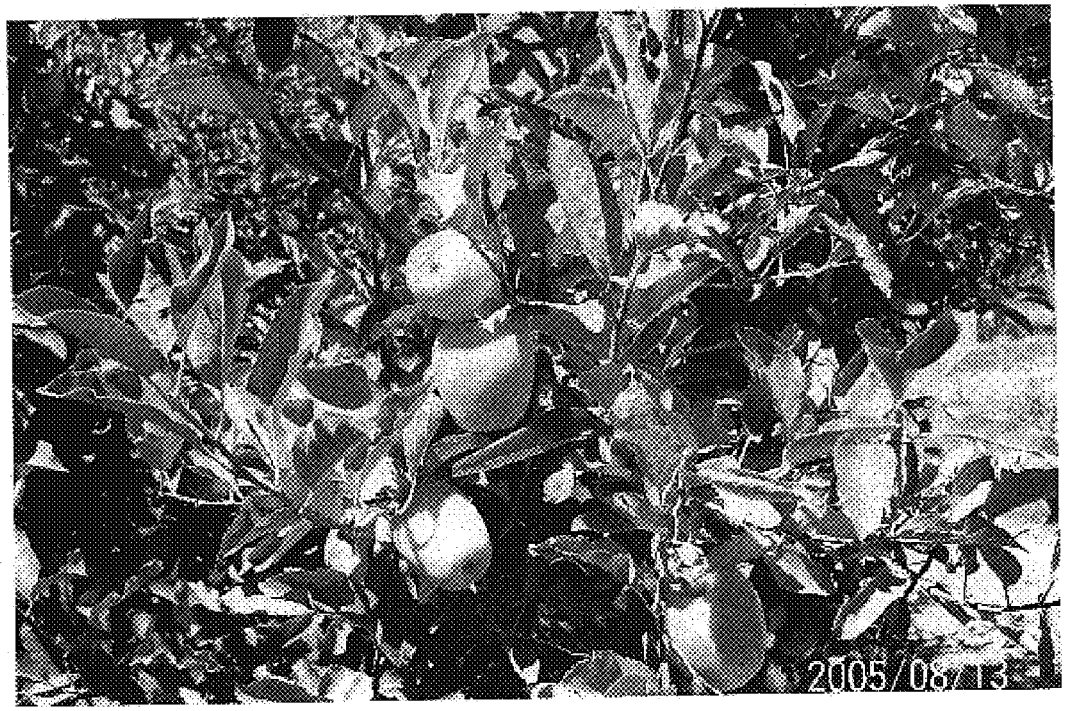
FIG. 2 shows the fruit on a 'Royal' Gala apple tree taken at the same time as the photograph of FIG. 1.
Figure 3:
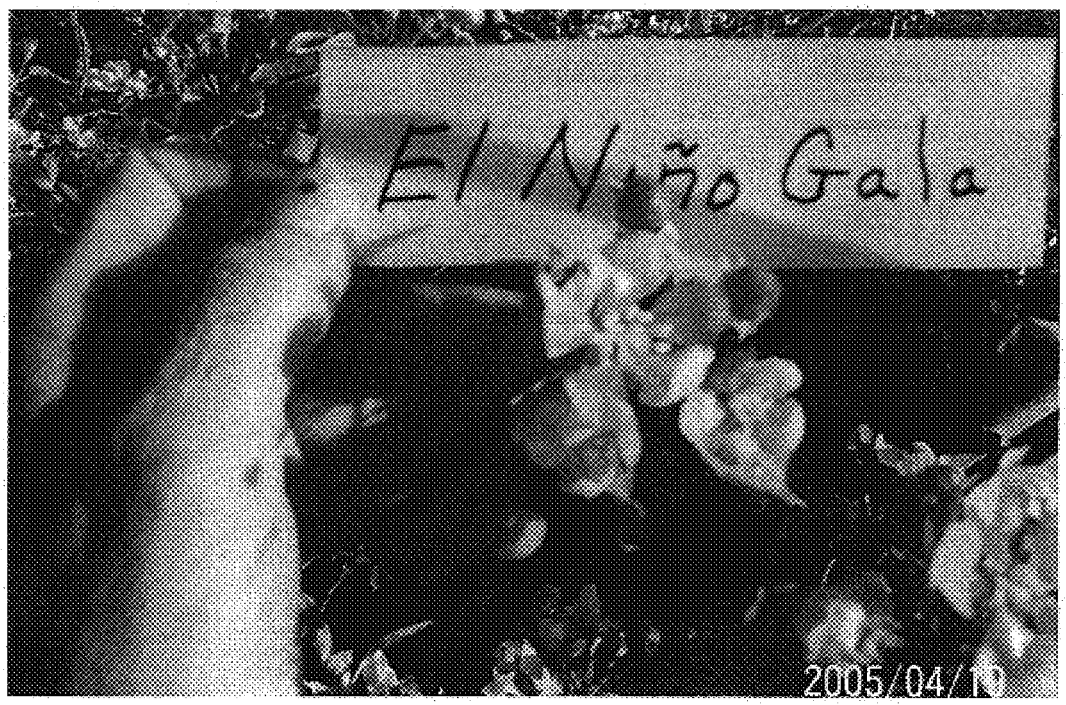
FIG. 3 shows blooms on one of the new 'El Niño' Gala apple trees.
Figure 4:
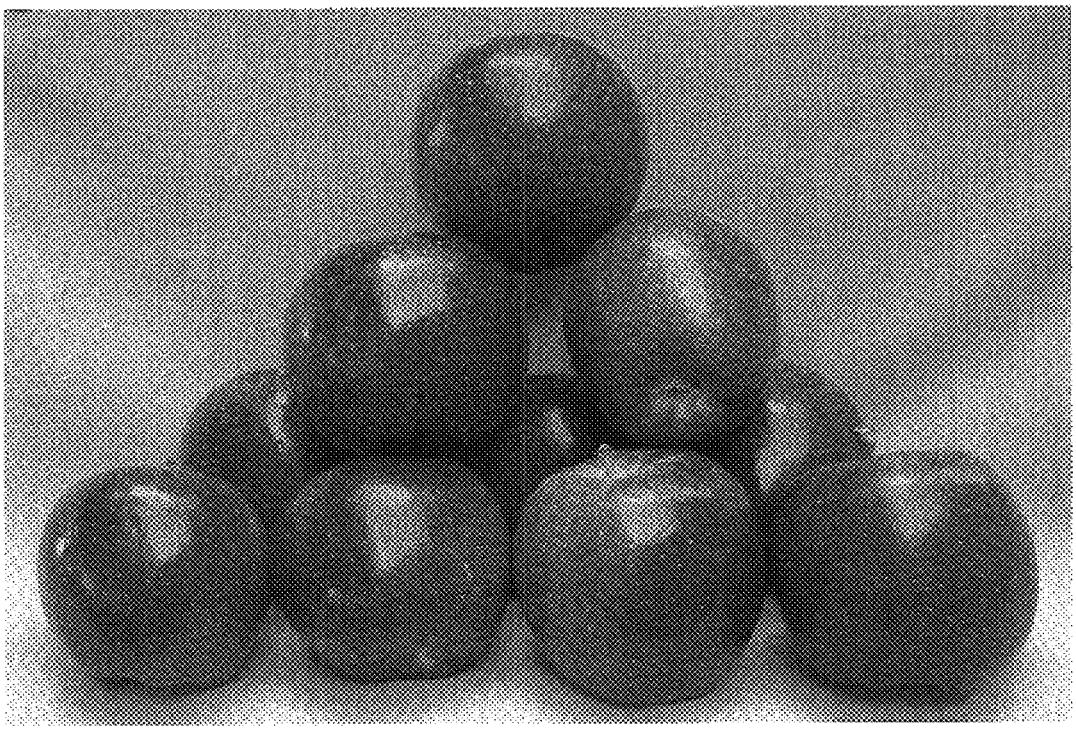
FIG. 4 illustrates exemplary fruit of the new variety at harvest maturity on Aug. 29, 2006, showing intense full color with darker stripes.

The fruit of 'El Niño' trees exhibits a size and shape that is typical of 'Royal Gala', but has intense dark red stripes over a bright red background skin color. 'El Niño' is usually colored by 90–100% red stripes and background. It should be noted that colors may vary, for example, due to lighting conditions at the time the photographs are taken. Therefore, color characteristics of this new variety should be determined with reference to the observations described herein, rather than from the photographs alone.

Scientific Name: *Malus domestica* 'El Niño'.
Parentage: Bud sport of 'Royal Gala'.
Botanical description:
Tree:
- *Vigor.*—Slightly weaker growth habit compared to, 'Royal Gala'. Fruit grows in spurs and short darts at close intervals across the limb. 'El Niño' has about a 85% growth vigor compared to 'Royal Gala' and Golden Delicious.
- *Overall shape.*—Conical, trained to a central leader.
- *Height.*—Height of the observed progeny was about 12 feet.
- *Width.*—Overall spread of the observed progeny trees was about 7 feet.

Trunk:
- *Trunk bark texture.*—Medium smooth to smooth.
- *Caliper.*—Original tree 4 inches, measured about 1 foot above ground.
- *Color.*—Tan-Brown, from the Greyed-Orange Group RHS N170A.
- *Lenticels.*—Present, moderate in number, medium small in size averaging 5–9 mm×1 mm. Dark brown from the Greyed-Orange Group RHS 165A.

Branches:
- *Branch pubescence.*—Light pubescence on one year growth.
- *Branch lenticels.*—Quantity: Medium density. About 12 per square inch. One-year old branches: Color: Brown, from the Greyed-Orange Group RHS N177A. Lenticels: Present and moderate in number, elongated, averaging 0.3×1.5 mm in size. Color is white. Two year old branches: Color: Brown, from the grey brown group RHS N199C. Lenticels: present and moderate in number, averaging 0.65×1.5 mm in size. Color is yellow white RHS 158C.

Internodes: Average internode length in one-year-shoot about 1⅛ inches.

Bearing: Arranged opposite with 8–16 leaves per one year old shoot.

Cold hardiness: Observed in Royal City, Wash., having a zipcode that places this location in USDA Zone 6b/7a.

Leaves (Observations from typical leaves):
- *Form.*—Medium long, oval, abruptly pointed.
- *Texture.*—Leathery.
- *Sheen.*—Bright.
- *Length.*—About 4½ inches to about 6 inches, averaging about 5½ inches.
- *Width.*—About 2 inches to about 3 inches, averaging about 2.5 inches.
- *Thickness.*—About 0.004 inch to about 0.006 inch, averaging about 0.005 inches.
- *Petiole.*—About 1.5 inches long; about 0.105 inch in diameter. Color of petiole is length green, greyed green group RHS 196A.
- *Margin.*—Crenate (bi-serrate).
- *Tip.*—Acute.
- *Leaf color.*—Upper surface is green, green group RHS 137B. Underside of leaf is green. Vein color is green, green group RHS 139D.
- *Stipules.*—Two stipules in opposite arrangement; lanceolate shape; average 2.5 mm×10 mm in size.
- *Pubescence.*—Present on under surface, moderate to heavy.

Flowers:

General: 'El Niño' attains full bloom 1 to 1½ days later than 'Royal Gala' in Grant County, Wash., with noticeably less "rat-tail" bloom on 1 year wood. As blooms open, the petals and spur leaves have a skinny, weak appearance with red pigment on the inside and outside of the petals. As the blooms continue to open, the petals and leaves are more similar to 'Royal Gala' and 'Gale Gala', except the petals are more reddish or pink. 'El Niño', thus far, has been much easier to blossom thin with lime sulphur than 'Royal Gala'.
- *Size.*—Medium size, typical flower measuring about 37 mm across.
- *Bud length.*—15 mm.
- *Bud diameter.*—10 mm.
- *Petals.*—Five petals per flower; about 0.6 (to slightly larger) inch long and 0.5 to slightly smaller) inch wide.
- *Stamen.*—14 stamens, each about 5 mm long.
- *Pistils.*—Stigma: About 7 mm long; 10 styles.
- *Sepals.*—About 7 mm long and about 5 mm wide.
- *Bloom season.*—In 2006, full bloom was observed in Grant County, Wash. on Apr. 28, 2006.

Fruit (Unless otherwise noted, from observations of a limited number of typical fruit in Grant County, Wash.):
- *Size.*—Medium to medium small, about 3 inches long and about 2⅞ to 3 inches across; average size of about 2¾ to 2⅞ to 3 inches.
- *Form.*—Oblique to ovate (round conical).
- *Cavity.*—Average width is 3.2 cm. Average depth is 1.5 cm.
- *Basin.*—About 0.4 to 0.5 inch deep and about 0.75 inch wide.
- *Skin appearance.*—Smooth.
- *Stem.*—Medium in length, typical average observed in August of about 0.8 inch to about 1.0 inch long and 0.125 inch in diameter. Stem is clubbed at the spur attachment.
- *Locules.*—Five.
- *Lenticels.*—Moderate in number at the basal end and becoming numerous in number at the apex end. Size range of 0.3–1 mm in diameter. White.
- *Color.*—General Color Effect: Dark red distinct stripe over red background over typically 95% to 100% of the surface. Dark red "chimera" over red under-stripes. Little ground color shows at harvest. As the ground turns from pale green to yellow in storage, the dark red pigment softens slightly, but remains distinctively dark red. Color is consistent throughout the tree. Striped over color is from the greyed purple group RHS 183A over RHS N34 of the orange red group. Where undercover is present, it appears to be yellow RHS 8A. Color development is slow, with the fruit appearing similar to 'Royal Gala' through July with a very dramatic color change the final 7–10 days before harvest. Color stability is excellent.

*Russetting.*—About 10% of fruit have varying degrees of stem bowl Russett.

Figure 5:
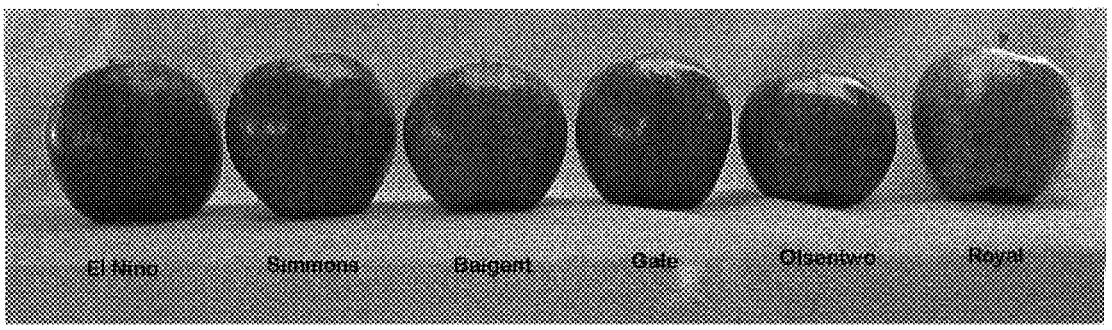
FIG. 5 illustrates fruit of the new variety and other identified Gala cultivars at harvest maturity on Aug. 29, 2006. Specimens were obtained from the original tree of the new 'El Niño' variety from an adjacent Royal Gala tree, and from the other selections from orchards located with an 18 mile radius of the original tree of the new variety with similar maturity dates.

Table 1 below shows a comparison table of average chroma and hue as measured by a Minolta colorimeter of the Gala cultivars illustrated in FIG. 5 at harvest maturity on Aug. 29, 2006. The patent status of the five other varieties mentioned in Table 1 is set forth in Table 2 below.

TABLE 1

| | 'El Nino' | 'Simmons' | 'Baigent' | 'Gale' | 'Olsen-two' | 'Royal' |
|---|---|---|---|---|---|---|
| Average Hue | 23.2 | 21.1 | 36.1 | 32.9 | 39 | 58.8 |
| Average Chroma | 35.6 | 39.6 | 40.8 | 44.3 | 40.9 | 37.5 |

TABLE 2

| U.S. Patent Status | |
|---|---|
| 'Royal Gala' | PP 4121 |
| 'Olsentwo Gala' | PP 9681 |
| 'Baigent Gala' | PP 10016 |
| 'Gale Gala' | PP 10114 |
| 'Simmons Gala' | PP 10840 |

Core: Core Line Attachment: medium.

*Core Position.*—Medium.

Cell: Tufted: yes, lightly.

*Cell shape.*—Round.

Tube: Funnel shaped.

Sepals: Downy.

Stamen position: Medium.

Axis: Axile and closed.

Seed: Number: one per cell.

*Shape.*—Obtuse.

*Color.*—Dark brown, RHS 166A.

Fruit properties at maturity (Based on 30 fruit tested in August 2005).

*Firmness.*—7.5 to 9 kg, averaging about 8.25 kg. Soluble solids: About 12–15%, averaging about 13.5%.

*Flavor.*—Typical of 'Royal Gala'.

*Juiciness.*—Similar to 'Royal Gala'.

*Aroma.*—Mildly aromatic, similar to 'Royal Gala'.

*Texture.*—Smooth and snappy crisp at maturity.

*Color.*—Light yellow group RHS 11D. A very light purple halo of color just beneath the skin to a maximum depth of 2 mm, RHS 185D.

*Flesh.*—Light yellow, RHS 11D. A very light purple halo of color just beneath the skin to a maximum depth of 2 mm, RHS 185D.

Fruit production: First picking date in 2005 in Grant County, Wash. was about Aug. 18, 2005. Average production about 90 pounds per tree.

Storage: Fruit remains fresh at room temperature for 10 days, and can be stored up to six months in cold storage (34° F.).

Usage: 92% fresh pack, 8% processor.

Fruit weight: Typically, 165–195 grams.

Horticultural characteristics—'El Niño' is similar to other Gala strains insofar as I have observed for mildew and pest susceptibility, frost tolerance, harvest timing, stem bowl cracking and sunburn. It's weak growth habit requires careful nutrition management.

I claim:

1. A new and distinct variety of apple tree named 'El Niño' substantially as illustrated and described.

* * * * *

UNITED STATES PATENT AND TRADEMARK OFFICE

CERTIFICATE OF CORRECTION

PATENT NO. : PP 18,512 P3
APPLICATION NO. : 11/501205
DATED : February 26, 2008
INVENTOR(S) : Steven A. McDonald It is certified that error appears in the above-identified patent and that said Letters Patent is hereby corrected as shown below:

In Column 1, line 4, please replace the paragraph "The entire disclosure of the provisional application is considered to part of the disclosure of the following application and is hereby incorporated by reference herein." with --This application claims the benefit of and priority to provisional plant patent application No. 60/709,892 filed on August 19, 2005. The entire disclosure of the provisional application is considered to be part of the disclosure of the following application and is hereby incorporated by reference herein.--.

In Column 2, line 13, please replace "applies" with --apples--.

In Column 3, line 20, please replace "to, 'Royal Gala'" with --to 'Royal Gala'--.

In Column 4, line 30, please replace "0.5 to" with --0.5 (to--.

Signed and Sealed this

Third Day of March, 2009

JOHN DOLL
*Acting Director of the United States Patent and Trademark Office*